United States Patent [19]

Takaichi et al.

[11] Patent Number: 5,160,728
[45] Date of Patent: Nov. 3, 1992

[54] PREPARATION FOR IRON SUPPLY, PREPARATION FOR VITAMIN SUPPLY AND METHOD FOR STABILIZING A FOAM PREPARATION

[75] Inventors: Akihisa Takaichi; Toshihiko Okamoto; Toshiaki Matsumoto, all of Tokushima, Japan

[73] Assignee: Otsuka Pharmaceutical Co., Ltd., Tokyo, Japan

[21] Appl. No.: 540,532

[22] Filed: Jun. 19, 1990

Related U.S. Application Data

[62] Division of Ser. No. 417,111, Oct. 4, 1989, Pat. No. 5,087,442.

[30] Foreign Application Priority Data

Oct. 4, 1988 [JP] Japan ............................... 63-250663
Dec. 2, 1988 [JP] Japan ............................... 63-306272

[51] Int. Cl.$^5$ .................... A61L 9/04; A61K 33/00; A61K 31/34; A61K 31/295
[52] U.S. Cl. ................................. 424/44; 424/715; 424/717; 514/474; 514/502; 514/574
[58] Field of Search ............. 424/43, 44, 715, 717; 514/474, 502, 574

[56] References Cited

U.S. PATENT DOCUMENTS

3,105,792 10/1963 White ............................ 424/715
4,265,847 5/1981 Hunt et al. ..................... 424/43

FOREIGN PATENT DOCUMENTS

2042323 3/1971 Fed. Rep. of Germany.
1338071 11/1973 United Kingdom.

OTHER PUBLICATIONS

Chemical Abstracts, vol. 110 (1989): "Effervescent tablets containing ferrous iron and ascorbic acid" Gergely et al.

Primary Examiner—Frederick E. Waddell
Assistant Examiner—Raymond J. Henley, III
Attorney, Agent, or Firm—Sughrue, Mion, Zinn, Macpeak & Seas

[57] ABSTRACT

There is described a preparation for iron supply comprising, as essential ingredients, a prescribed iron containing compound, sodium carbonate or sodium hydrogencarbonate and a neutralizing agent. This preparation is easily dissolved in water, and has a good taste so that it is agreeable to drinking, whereby sufficient amount of iron can suitably supplied to the living body. Also, there is described a preparation for iron supply or vitamin supply, to which potassium carbonate is added as a reservation stabilizing agent.

27 Claims, No Drawings

PREPARATION FOR IRON SUPPLY, PREPARATION FOR VITAMIN SUPPLY AND METHOD FOR STABILIZING A FOAM PREPARATION

This is a divisional of Application Ser. No. 07/417,111, filed Oct. 4, 1989 now U.S. Pat. No. 5,087,442.

BACKGROUND OF THE INVENTION

This invention relates to a preparation for iron supply, a preparation for vitamin supply and a method for stabilizing a foam preparation, which are capable of supplying iron or vitamins to a living body.

In the living body, iron is important as an essential element of hemoglobin, and normal man ordinally intakes the necessary amount of iron from food. That is to say, iron is absorbed in the bivalent form into all digestive tubes, especially the small intestine (mainly the duodenum), then is oxided to the tervalent form in a mucosa cell, and enters the blood stream to bond with transferrin ($\beta_1$-globulin) which is a carrier protein, thereby transferred to the liver, pancreas, bone marrow and the like which are storage organs.

It is said that an excretion amount of iron per day in the normal man is about 0.5 to 1 mg. This excretion amount means the necessary intake amount per day of man.

In general, however, the absorption rate of iron from food is a low level of several percents. Due to this low absorption rate, the living body frequently falls into an extraphysiologic state such as iron deficiency anemia. As example of iron deficiency anemia, green sickness (chlorosis), catapletic hypochromic anemia, hypochromic anemia in gestation, hypochromic anemia in gastrointestinal disease and the like are known.

Recently, for the purpose of improvement of such extraphysiologic state, i.e. prevention and therapy of anemia, various iron compound preparations (hematinics) are known. For example, DE 3632334 A1 discloses an oral administration iron preparation and a foam tablet basing the same, including iron gluconate as a water soluble iron salt, ascorbic acid, and $CO_2$ generating compound, e.g. sodium bicarbonate, sodium carbonate.

However, the foam tablet containing iron gluconate is inferior in water solubility, and therefore it takes a fairly long time from putting it into water to taking it. Also, the above foam tablet tastes bad, so that it is hard to drink. Furthermore, since the water content of iron gluconate is comparatively large, i.e. 6.5 to 10% (dihydrate), the foam tablet has a disadvantage in that it takes a fairly long time to dry the tablet in a process for manufacturing, or that in the process employing a drying step, e.g. a process employing a method for directly pessurizing powder, method for dry pressurizing granules or the like, a troublesome problem occurs in that water included in materials should be sufficiently lowered. If removing water is insufficient, foaming of the tablet occurs. Accordingly, the drying step becomes troublesome, and further the use of a drying device results in complications. A similar problem also occurs in a foam tablet for supplying vitamin such as vitamin C, and it is inferior in reservation stability, even if using a drying agent.

SUMMARY OF THE INVENTION

An object of this invention is to provide a preparation for iron supply which has a good taste, and intake or dosing is easy.

Another object of this invention is to provide a preparation for iron supply which is excellent in solubility or dispersion to water, and therefore is dissolved or dispersed in water easily and rapidly, thereby being suitable to take orally.

Still another object of this invention is to provide a preparation for iron supply which can stably supply a sufficient amount of iron to the living body.

A further object of this invention is to provide a preparation for vitamin supply and a method for stablizing the foam preparation supplying iron or vitamins, which is excellent in terms of preservation stability for a long period of time, and a drying step in the manufacturing process becomes easy.

According to this invention, there is provided a preparation for iron supply comprising, as essential ingredients, 0.01 to 3.5% by weight, as converted into iron, of at least one iron containing compound selected from the group consisting of ammonium iron citrate, sodium ferrous citrate and iron citrate, 10 to 35% by weight of sodium carbonate and/or sodium hydrogencarbonate, and 20 to 70% by weight of a neutralizing agent.

The prepation of this invention is mainly used in the form of tablet.

An iron salt of citric acid which is used as iron containing compound, has better taste than various other iron containing compound such as iron gluconate. Therefore, the preparation of this invention containing this iron salt can be easily drunk. Also, since an iron salt of citric acid in this invention has excellent solubility, the preparation is easily and rapidly dissolved in water by merely putting into water when using, with generating carbonic acid gas due to neutralization (ordinally, dissolving whithin 2 minutes at 6° to 10° C.). Accordingly, there is not a troublesomely long waiting time for dissolving. In addition, the iron salt of citric acid has a higher iron content than iron gluconate, and therefore it is possible to supply and absorb enough content of iron to living body, whereby the nutrition effect and therapy, effect against anemia are expected. Also, since the iron salt of citric acid has a low water content, e.g., water content of ammonium iron citrate is not more than 5%, whereas iron gluconate is 6.5 to 10%, the drying step in the manufacturing process can be easily and rapidly carried out.

According to this invention, there is also provided a preparation for iron supply comprising, as essential ingredients, an iron containing compound, sodium carbonate and/or sodium hydrogencarbonate, a neutralizing agent and potassium carbonate which is a stabilizing agent. Furthermore, there is also provided a preparation for vitamin supply which employs vitamin C or the like instead of a part of the iron compound or neutralizing agent mentioned above.

Potassium carbonate used in these preparations has advantages in that the stability during preservation of the foam preparation is secured, and especially degeneration of the preparation in the presence of water can be prevented.

Accordingly, there is also provided a method for stabilizing a foam preparation which comprises adding potassium carbonate to a foam preparation to prevent degeneration of the foam preparation.

DETAILED DESCRIPTION OF THE INVENTION

It is preferred that the iron containing compound used in this invention, which is ammonium iron citrate, sodium ferrous citrate or iron citrate, is a powder of which diameter is not more than 200 μm, in view of solubility and the blending property in the manufacturing process. One or more than two of the above iron containing compounds may be used.

In such a case, the amount of iron containing compound to be blended is 0.01 to 3.5% by weight, preferably 0.06 to 0.6% by weight as converted to iron per one preparation. As a result, the obtained preparation has an excelent iron supply effect. As an especially preferred amount of each iron containing compound to be blended, 0.6 to 1.8% by weight of ammonium iron citrate; 0.6 to 3.0% by weight of sodium ferrous citrate; and 0.4 to 1.8% by weight of iron citrate are employed.

Sodium carbonate and/or sodium hydrogencarbonate, and neutralizing agent are blended as a foam component in addition to the above iron containing compound. The neutralization agent is acid compound capable of neutralizing sodium carbonate and sodium hydrogencarbonate to generate carbnonic acid gas. An example of such a neutralizing agent is an organic acid such as L-tartaric acid, citric acid, fumaric acid or ascorbic acid.

The amount of the above foam component to be blended is decided so that the solution obtained by dissolving in water indicates acid, especially about 3.5 to 4.6 of pH in view of solubility and taste of the solution. As more concrete explanation of the blending amount of each ingredient, sodium carbonate and/or sodium hydrogencarbonate is 10 to 35% by weight, and neutralizing agent is 20 to 70% by weight per one preparation. Especially, sodium carbonate is selected from the range of 11 to 31% by weight, preferably 22 to 26% by weight, sodium hydrogencarbonate is selected from the range of 10 to 35% by weight, preferably 20 to 30% by weight, and especially it is most preferable in view of solubility and taste that sodium hydrogencarbonate is used alone in the range of 20 to 25% by weight.

It is suitable that the neutralizing agent is blended in the range of 20 to 70% by weight, preferably 30 to 40% by weight per one preparation, and especially it is most preferable in view of solubility, taste and iron absorption to use a combination of 18 to 25% by weight of L-tartaric acid and 8 to 22% by weight of L-ascorbic acid.

According to this invention, in addition to sodium carbonate or sodium hydrogencarbonate and neutralizing agent blended as a foam component, it is preferred that potassium carbonate is blended as a preservation stabilizing agent. That is to say, since sodium carbonate or sodium hydrogencarbonate is neutralized in the presence of water by a neutralizing agent, such as organic acid to generate carbonic acid gas and promote the degradation and solubility of the tablet, preservation of the preparation should keep a dry condition as much as posible so as to prevent the occurrence of foam. There, however, is the possibility of foaming during preservation due to the presence of water remaining in the preparing process or water of crystallization, even if it is preserved in a sealed container together with drying agent, since the obtained composition is highly hygroscopic, and carbonate salt and neutraizing agent mentioned above are in the condition that reaction of them is easily occured. If carbonic acid gas is generated during preservation, the inner pressure of the sealed container is increased. This results in deformation or damage of the container, or a cause that when using, the product is not foamed. Foaming during preservation is accelerated under a high temperature condition, and further the generated reaction water and carbonic acid gas accelerates the reaction.

It is now found that potassium carbonate is very effective to prevent foam during preservation as mentioned above, and even if a drying agent is not used during preservation, foam and deterioration of quality, e.g. changing color, taste or soluble time of the preparation, can be prevented. In view of securing a high stability of the preparation and easily taking it without lowering taste, it is suitable that potassium carbonate is added at the amount of 0.2 to 13% by weight, preferably 0.3 to 3% by weight, more preferably 0.4 to 1% by weight per one preparation. Potassium carbonate to be added is preferably used in the form of anhydrous $K_2CO_3$.

Such a preservation stabilizing agent is not only applied to an iron supply preparation including citrate type iron compounds, but also is applied to other preparations including other iron compounds such as ferrous gluconate, ferrous pyrophosphate, iron lactate, ferrous sulfate, iron trichloride or the like, and further can be applied to a foam preparation for supplying nutrition including vitamin C instead of the iron containing compound. The amount of vitamin C to be added is not limited, and is suitablly selected from the range not exceed 30% by weight, preferably about 5 to 25% by weight.

To these preparations in this invention, if necessary, various additives ordinarily known, such as vehicle, binding agent, disintegrator, lubricant, thickener, surface active agent, osmotic pressure adjusting agent, electrolyte, sweetening agent, perfume, coloring matter, pH adjusting agent or the like, can be added, in addition to the above iron containing compound or vitamin C and foam ingredients. Examples of the vehicle are starches such as wheat starch, potato starch, coan starch, dextrin; sugars such as cane sugar, grape sugar, fruit sugar, malt sugar, xylose, milk sugar, or the like; sugaralcohol such as sorbitol, mannitol, multitol, xylitol, or the like; sugar inverted glycoside such as coupling sugar, palatinose or the like; calcium phosphate; calcium sulfate; or the like. Examples of the binding agent or thickener are starch, various sugars, gelatin, gum arabic, dextrin, methyl cellulose, CMC-Na, polyvinyl pyrrolidone, polyvinyl alcohol, hydroxypropyl cellulose, xanthan gum, pectin, tragacanth gum, casein, alginic acid, or the like. Examples of lubricant are leucine, isoleucine, L-valine, sugar-ester, hardened oil, stearic acid, magnesium stearate, talc, macrogol or the like. Examples of disintegrator are avicel, CMC, CMC-Ca or the like. Examples of surface active agent are polysorbate, lecithin or the like. Examples of sweetening agent are various sugars; various sugaralcohol; dipeptide such as aspartame, alitame; stevia; saccharin; or the like. Suitable amounts of these additives are decided in view of relation to essential ingredients, properties of the preparations, process for preparing it or the like.

Furthermore, the suitable amount of various vitamin, especially cyanocobalamin, ascorbic acid (vitamine C) or the like may be added to the preparation for iron supply. Vitamin C is not only an antioxidant, but also enhances the iron supply effect due to increasing the absorption of the iron containing compound to the living body, and simultaneously is supplied to the living body.

In preparing the preparation of this invention, the similar method to the ordinary method for preparing this sort of preparation such as foam preparation may be employed. That is, it can be prepared by a method for directly pressurizing powders or a method for wet pressurizing granule, after weighing and mixing the prescribed amount of each ingredient.

The preparation of this invention, such as foam tablet, thus obtained is changed to the drinking form by merely putting into water, whereby it can be orally taken with ease.

The dose should be decided in compliance with age, sex, weight, the degree of disease or the like, and accordingly is not limited. In general, one tablet is prepared at about 1.5 to 6 g of weight. One or two tablets may be taken at a time by dissolving in 100 to 300 ml of water.

The preferred composition of the preparation of iron supply is exemplified below.

| (Ingredient) | (Amounts) |
|---|---|
| Blend example 1 | |
| Iron containing compound | 0.4 to 3% |
| Sodium hydrogencarbonate | 20 to 25% |
| L-Tartaric acid | 18 to 25% |
| Ascorbic acid | 8 to 22% |
| Blend example 2 | |
| Iron containing compound | 0.4 to 3% |
| Sodium hydrogencarbonate | 20 to 25% |
| Potassium carbonate | 0.3 to 3% |
| L-Tartaric acid | 18 to 25% |
| Ascorbic acid | 8 to 22% |

EXAMPLES

Examples of this invention are explained below in detail. In each example, parts and % mean parts by weight and % by weight, respectively, except for special remarks.

EXAMPLES 1 TO 18 (PREPARATION OF IRON SUPPLY)

After mixing each ingredient shown in Table 1, by preparing the mixture in accordance with a method for directly pressurizing powder, foam tablets were obtained.

TABLE 1

| Ingredients | 1 | 2 | 3 | 4 | 5 | 6 | 7 | 8 | 9 | 10 | 11 | 12 |
|---|---|---|---|---|---|---|---|---|---|---|---|---|
| Glanulated sugar (parts) | 38 | 37 | 38 | 39 | 14 | 40 | 38 | 37 | 38 | 34 | 32 | 28 |
| Wheat starch (parts) | — | — | — | — | — | — | — | — | — | 4 | 1 | — |
| Dextrin (parts) | — | — | — | — | — | — | — | — | — | — | 5 | — |
| L-Ascorbic acid (parts) | 12 | 12 | 12 | 12 | 17 | 12 | 12 | 12 | 12 | 12 | 12 | 9 |
| L-Tartaric acid (parts) | 23 | 23 | 23 | 23 | 32 | — | 23 | 23 | 23 | 23 | 32 | 37 |
| Citric acid (parts) | — | — | — | — | — | 21 | — | — | — | — | — | — |
| Aspartame | | | | | | | | | | | | |
| (parts) | 0.8 | 0.8 | 0.8 | 0.8 | 1 | 0.9 | — | 0.8 | 0.8 | 0.8 | 0.8 | 0.7 |
| (parts) | — | — | — | — | — | — | 0.1 | — | — | — | — | — |
| NaHCO$_3$ (parts) | 23 | 23 | 23 | 23 | 23 | 23 | 23 | 23 | 23 | 23 | 23 | — |
| Na$_2$CO$_3$ (parts) | — | — | — | — | — | — | — | — | — | — | — | 23 |
| Ammonium iron citrate (parts) | 0.8 | 1.7 | 0.6 | 0.3 | 1.2 | 0.8 | 0.8 | — | — | 0.8 | 0.8 | 0.7 |
| Sodium ferrous citrate (parts) | — | — | — | — | — | — | — | 1.4 | — | — | — | — |
| Iron citrate (parts) | — | — | — | — | — | — | — | — | 0.8 | — | — | — |
| Cyanocobalamin (parts) | * | * | * | * | * | * | * | * | * | * | * | * |
| Perfume and coloring matter (parts) | ** | ** | ** | ** | ** | ** | ** | ** | ** | ** | ** | ** |
| Preparation weight (g/one tablet) | 4.2 | 4.2 | 4.2 | 4.2 | 3.0 | 4.2 | 4.2 | 4.2 | 4.2 | 4.2 | 4.2 | 5.4 |
| Iron content/one tablet (mg) | 6 | 12 | 4 | 2 | 6 | 6 | 6 | 6 | 6 | 6 | 6 | 6 |

| Ingredients | 13 | 14 | 15 | 16 | 17 | 18 |
|---|---|---|---|---|---|---|
| Glanulated sugar (parts) | 45 | 40 | 43 | 27 | 34 | 26 |
| Wheat starch (parts) | — | — | — | — | — | — |
| Dextrin (parts) | — | — | — | — | — | — |
| L-Ascorbic acid (parts) | — | 9 | 13 | 12 | 12 | 12 |
| L-Tartaric acid (parts) | 28 | 24 | 18 | 29 | 22 | 22 |
| Citric acid (parts) | — | — | — | — | — | — |
| Aspartame | | | | | | |
| (parts) | 0.8 | 0.9 | 0.9 | 0.9 | 0.8 | 0.8 |
| (parts) | — | — | — | — | — | — |
| NaHCO$_3$ (parts) | 24 | 24 | 21 | 29 | 23 | 23 |
| Na$_2$CO$_3$ (parts) | — | — | — | — | — | — |
| Ammonium iron citrate (parts) | 0.8 | 0.8 | 0.9 | 0.8 | 6.8 | 14 |
| Sodium ferrous citrate (parts) | — | — | — | — | — | — |
| Iron citrate (parts) | — | — | — | — | — | — |
| Cyanocobalamin (parts) | * | * | * | * | * | * |
| Perfume and coloring matter (parts) | ** | ** | ** | ** | ** | ** |
| Preparation weight (g/one tablet) | 4.2 | 4.2 | 3.8 | 4.2 | 4.3 | 4.3 |
| Iron content/one tablet (mg) | 6 | 6 | 6 | 6 | 50 | 100 |

*indicates "a trace amount of cyanocobalamin"
**Indicates "a suitable amount of perfume and coloring matter"

| (Ingredient) | (Amounts) |
|---|---|
| Blend example 1 | |
| Iron containing compound | 0.4 to 3% |
| Sodium hydrogencarbonate | 20 to 25% |
| L-Tartaric acid | 18 to 25% |

EXAMPLES 19 TO 26 (INCLUDING POTASSIUM CARBONATE)

Foam tablets having the composition shown in Table 2 were prepared by using the similar method of Examples 1 to 18.

TABLE 2

| Ingredients | 19 | 20 | 21 | 22 | 23 | 24 | 25 | 26 |
|---|---|---|---|---|---|---|---|---|
| Glanulated sugar (%) | 40 | 40 | 40 | 40 | 40 | 40 | 40 | 35 |
| L-Ascorbic acid (%) | 11 | 11 | 11 | 11 | 11 | 11 | 11 | 13 |
| L-Tartaric acid (%) | 23 | 23 | 23 | 23 | 23 | 23 | 23 | 25 |
| Sweetening (%) | ** | ** | ** | ** | ** | ** | ** | ** |
| $NaHCO_3$ (%) | 22 | 22 | 22 | 21 | 20 | 21 | 21 | 11 |
| Ammonium iron citrate (%) | 0.8 | 0.8 | 0.8 | 0.8 | 0.8 | — | — | 0.7 |
| Sodium ferrous citrate (%) | — | — | — | — | — | 1.2 | — | — |
| Iron citrate (%) | — | — | — | — | — | — | 0.8 | — |
| Cyanocobalamin (%) | * | * | * | * | * | * | * | * |
| Sodium citrate (%) | ** | ** | ** | ** | ** | ** | ** | ** |
| Perfume and coloring matter (%) | ** | ** | ** | ** | ** | ** | ** | ** |
| Potassium carbonate (%) | 0.3 | 0.4 | 0.5 | 1.0 | 2.0 | 0.5 | 0.5 | 13 |
| TOTAL (g) | 4.5 | 4.5 | 4.7 | 4.6 | 4.5 | 4.7 | 4.7 | 5.4 |

*indicates "a trace amount"
**Indicates "a suitable amount"

STABILITY TEST

A comparative test between the tablet having a composition obtained by in Example 20 and the tablet having the same composition as in Example 20 except for not adding potassium carbonate was carried out. In the test, each tablet was wrapped by in a wrapping sheet (alminium laminated glassine paper), and was stored in a constant temperature room kept at 37° C.

(i) Swelling test of wrapping sheet

The gas generated in each sheet wrapping the tablet was taken out every prescribed term, and was measured by a measuring cylinder.

Test result is shown in Table 3.

TABLE 3

| Storage term (months) | Amount of gas (ml) | |
|---|---|---|
| | Tablet not adding $K_2CO_3$ | Tablet adding $K_2CO_3$ (0.4%) |
| 0 | 2.5 | 2.5 |
| 1 | 3.2 | 2.6 |
| 2 | 5.5 | 2.6 |
| 3 | 6.2 | 2.6 |

(ii) Discoloration test of tablets

The color difference of the surface of each tablet was measured every prescribed term by a color-difference meter (COLOR ACE MODEL TC-1 manufactured by Tokyo Densyoku Co., Ltd., Japan). Test results are shown in Table 4.

The color difference was indicated in comparison with a tablet, which was stored at 4° C. without testing after preparing, as a control, by NBS (National Bureau of Standard) unit (value of $\Delta E$ = Color difference). It is said that this unit corresponds well with the sensible coloring difference. The relation between NBS unit and sense is as follows:

| (NBS unit) | (Difference of sense) |
|---|---|
| 0 to 0.5 | Trace |
| 0.5 to 1.5 | Slight |
| 1.5 to 3.0 | Noticeable |
| 3.0 to 6.0 | Appreciable |
| 6.0 to 12.0 | Much |
| more than 12.0 | Very much |

TABLE 4

| Storage term (months) | color difference | |
|---|---|---|
| | Tablet not adding $K_2CO_3$ | Tablet adding $K_2CO_3$ (0.4%) |
| 1 | 3.31 | 1.11 |
| 2 | 6.26 | 1.64 |
| 3 | 12.82 | 1.99 |

Furthermore, the degree of discoloration was examined by L. a. b. The test results are shown in Table 5. In Table 5, High value of "L" means high brightness. High value of (+) side of "a" means high degree of red, and high value of (−) side of "a" means high degree of green. High value of (+) side of "b" means high degree of yellow, and high value of (−) side of "a" means high degree of blue.

TABLE 5

| Storage term (month) | Tablet not adding $K_2CO_3$ | | | Tablet adding $K_2CO_3$ (0.4%) | | |
|---|---|---|---|---|---|---|
| | L | a | b | L | a | b |
| 0 | 76.18 | 1.15 | 12.98 | 75.18 | 1.23 | 11.50 |
| 1 | 73.79 | 3.02 | 11.68 | 74.80 | 2.10 | 10.93 |
| 2 | 70.27 | 2.53 | 14.50 | 76.82 | 1.30 | 11.58 |
| 3 | 63.63 | 3.20 | 14.57 | 74.06 | 2.83 | 11.13 |

(iii) solubility test

Each tablet was put into 140 ml of cooled water of 8° to 9° C., and the time to necessary for completely dissolving was measured. The test results are shown in Table 6.

TABLE 6

| Storage term (months) | Dissolving time | |
|---|---|---|
| | Tablet not adding $K_2CO_3$ | Tablet adding $K_2CO_3$ (0.4%) |
| 0 | 2' 10" | 1' 43" |
| 1 | 2' 40" | 1' 50" |
| 2 | 2' 55" | 1' 55" |
| 3 | 3' 00" | 1' 55" |

In Table, mark ' means "minute", and mark " means "second".

(iv) Taste changing test

The change of taste was estimated by a sensual test in comparison with the tablet which was stored at 4° C. without testing after preparing. The test results are shown in Table 7. The estimation is carried out by the following 5 steps with 2 men.

| (Points) | (Content of estimation) |
|---|---|
| 1 | Not changed |
| 2 | Slightly changed, but not problemed |
| 3 | Recognizably changed |
| 4 | Apparently recognizable change |
| 5 | Very much changed |

TABLE 7

| Storage term (months) | Points of estimation | |
|---|---|---|
| | Tablet not adding $K_2CO_3$ | Tablet adding $K_2CO_3$ (0.4%) |
| 1 | 2 | 1 |
| 2 | 3 | 1 |
| 3 | 5 | 2 |

As apparent from these test results, the stabilizing effect is recognized in all test items by adding $K_2CO_3$.

EXAMPLE 27 (PREPARATION FOR VITAMIN SUPPLY)

A foam tablet having the following composition was prepared by using a similar method to Examples 1 to 18.

| (Ingredients) | (%) |
|---|---|
| Purified white sugar | 33.9 |
| L-Ascorbic acid | 21 |
| L-Tartaric acid | 20 |
| Aspartame | suitable amount |
| Sodium hydrogencarbonate | 21 |
| Sodium chloride | suitable amount |
| Potassium carbonate | 0.5 |
| Perfume | suitable amount |
| Total | 100 |

EXAMPLE 28 (preparation for vitamin supply)

A foam tablet having the following composition was prepared by using a similar method to Examples 1 to 18.

| (Ingredients) | (%) |
|---|---|
| Purified white sugar | 41.3 |
| L-Ascorbic acid | 10 |
| L-Tartaric acid | 23 |
| Aspartame | suitable amount |
| Sodium hydrogencarbonate | 22 |
| Sodium citrate | suitable amount |
| Potassium carbonate | 0.4 |
| Perfume | suitable amount |
| Total | 100 |

The preparations of Examples 27 and 28 also show almost the same high stabilizing effect as the above Examples due to adding potassium carbonate.

What is claimed is:

1. In a foam preparation comprising a foaming effective amount of sodium carbonate or sodium hydrogencarbonate, and a neutralizing effective amount of a neutralizing agent, wherein the neutralizing agent is an acid compound which neutralizes said sodium carbonate and/or sodium hydrogencarbonate to generate acid gas, the improvement comprising a storage stabilizing effective amount of potassium carbonate in said foam preparation.

2. A method for stabilizing a foam preparation which consists essentially of:
   (A) adding a storage stabilizing effective amount of potassium carbonate to a foam preparation comprising:
     (i) a foaming effective amount of sodium carbonate or sodium hydrogencarbonate; and
     (ii) a neutralizing effective amount of a neutralizing agent, wherein the neutralizing agent is an acid compound which neutralizes said sodium carbonate and/or sodium hydrogencarbonate to generate carbonic acid gas; and
   (B) storing the foam preparation.

3. The method for stabilizing a foam preparation according to claim 2, wherein the amount of said sodium carbonate employed is in the range of from 11 to 31% by weight.

4. The method for stabilizing a foam preparation according to claim 3, wherein the amount of said sodium carbonate employed is in the range of from 22 to 26% by weight.

5. The method for stabilizing a foam preparation according to claim 2, wherein the amount of said sodium hydrogencarbonate employed is in the range of from 20 to 30% by weight.

6. The method for stabilizing a foam preparation according to claim 2, wherein the amount of said neutralizing agent employed is in the range of from 30 to 40% by weight.

7. The method for stabilizing a foam preparation according to claim 2, wherein the neutralizing agent is ascorbic acid and/or L-tartaric acid.

8. The method for stabilizing a foam preparation according to claim 7, wherein the amounts of said ascorbic acid and said L-tartaric acid employed is in the ranges of from 8 to 22% by weight and 18-25% by weight, respectively.

9. The method for stabilizing a foam preparation according to claim 2, wherein the amount of said potassium carbonate employed is in the range of from 0.2 to 13% by weight.

10. The method for stabilizing a foam preparation according to claim 9, wherein the amount of said potassium carbonate employed is in the range of from 0.3 to 3% by weight.

11. The method for stabilizing a foam preparation according to claim 10, wherein the amount of said potassium carbonate employed is in the range of from 0.4 to 1% by weight.

12. The method for stabilizing a foam preparation according to claim 2, wherein the foam preparation additionally contains 0.01 to 3.5% by weight, in terms of iron, of at least one iron-containing compound selected from the group consisting of ammonium iron citrate, sodium ferrous citrate and iron citrate.

13. The method for stabilizing a foam preparation according to claim 2, wherein the foam preparation contains at least Vitamin C as the neutralizing agent.

14. The method for stabilizing a foam preparation according to claim 2, wherein the amount of said sodium carbonate or sodium hydrogencarbonate employed is in the range of 10 to 35% by weight.

15. The method for stabilizing a foam preparation according to claim 2, wherein the amount of said neutralizing agent employed is in the range of 20 to 70% by weight.

16. The foam preparation according to claim 1, wherein the foam preparation contains at least Vitamin C as a neutralizing agent.

17. The foam preparation according to claim 1, wherein the amount of said potassium carbonate employed is in the range of from 0.2 to 13% by weight.

18. The foam preparation according to claim 17, wherein the amount of said potassium carbonate employed is in the range of from 0.3 to 3% by weight.

19. The foam preparation according to claim 18, wherein the amount of said potassium carbonate employed is in the range of from 0.4 to 1% by weight.

20. The foam preparation according to claim 1, wherein the amount of said sodium carbonate or sodium hydrogencarbonate employed is in the range of from 10 to 35% by weight.

21. The foam preparation according to claim 20, wherein the amount of said sodium hydrogencarbonate employed is in the range of from 20 to 30% by weight.

22. The foam preparation according to claims 20, wherein the amount of sodium carbonate employed is in the range of from 11 to 31% by weight.

23. The foam preparation according to claims 22, wherein the amount of sodium carbonate employed is in the range of from 22 to 26% by weight.

24. The foam preparation according to claim 1, wherein the amount of said neutralizing agent employed is in the range of from 20 to 70% by weight.

25. The foam preparation according to claim 24, wherein the amount of said neutralizing agent employed is in the range of from 30 to 40% by weight.

26. The foam preparation according to claim 1, wherein the neutralizing agent is ascorbic acid and/or L-tartaric acid.

27. The foam preparation according to claim 26, wherein the amounts of said ascorbic acid and/or said L-tartaric acid employed is in the range of from 8 to 22% by weight and 18 to 25% by weight, respectively.

* * * * *